(12) United States Patent
Gafoor et al.

(10) Patent No.: US 12,285,579 B2
(45) Date of Patent: Apr. 29, 2025

(54) SHEATH STEPWISE DILATION

(71) Applicant: EvolutionMedVentures LLC, Plymouth, MN (US)

(72) Inventors: Sameer Gafoor, Mercer Island, WA (US); Ahmed Elmouelhi, Plymouth, MN (US)

(73) Assignee: EVOLUTIONMEDVENTURES LLC, Plymouth, MN (US)

( * ) Notice: Subject to any disclaimer, the term of this patent is extended or adjusted under 35 U.S.C. 154(b) by 0 days.

(21) Appl. No.: 18/644,227

(22) Filed: Apr. 24, 2024

(65) Prior Publication Data

US 2024/0269442 A1    Aug. 15, 2024

Related U.S. Application Data

(63) Continuation of application No. 17/858,349, filed on Jul. 6, 2022, now Pat. No. 11,998,709, which is a continuation of application No. 17/524,260, filed on Nov. 11, 2021, now Pat. No. 11,439,800.

(60) Provisional application No. 63/113,921, filed on Nov. 15, 2020.

(51) Int. Cl.
*A61M 29/00* (2006.01)
*A61M 25/00* (2006.01)
*A61M 25/09* (2006.01)

(52) U.S. Cl.
CPC ............ *A61M 29/00* (2013.01); *A61M 25/09* (2013.01); *A61M 2025/0006* (2013.01)

(58) Field of Classification Search
CPC .. A61M 25/0662; A61M 25/09; A61M 25/10; A61M 25/10181; A61M 25/1018; A61M 29/00; A61M 29/104; A61M 2025/0006; A61M 2025/1059

USPC ......................................................... 606/191
See application file for complete search history.

(56) References Cited

U.S. PATENT DOCUMENTS

| 4,385,631 A | 5/1983 | Uthmann |
| 5,405,329 A | 4/1995 | Durand |
| 8,317,715 B2 * | 11/2012 | Belleville ............. A61M 25/00 600/485 |

(Continued)

FOREIGN PATENT DOCUMENTS

EP    692273 A1    1/1996

OTHER PUBLICATIONS

European Patent Office "Extended European Search Report" From Application No. 21892789.5, Dated Oct. 9, 2024, pp. 10.

*Primary Examiner* — Jocelin C Tanner
(74) *Attorney, Agent, or Firm* — Fredrikson & Byron, P.A.

(57) ABSTRACT

A sheath assembly includes a first sheath, a second sheath, and an attachment mechanism. The first sheath includes a first sheath inner surface defining a first sheath lumen extending along a first sheath central longitudinal axis between a first sheath first end portion and a first sheath second end portion. The second sheath includes a second sheath inner surface defining a second sheath lumen extending along a second sheath longitudinal axis between a second sheath first end portion and a second sheath second end portion. The attachment mechanism couples the second sheath to the first sheath. The attachment mechanism includes an attachment mechanism step-up dilation. At least a portion of the attachment mechanism is asymmetrical, at the attachment mechanism step-up dilation, about the first sheath central longitudinal axis.

20 Claims, 7 Drawing Sheets

(56) References Cited

U.S. PATENT DOCUMENTS

2012/0259208 A1 10/2012 Bloom et al.
2015/0217084 A1 8/2015 Tassoni, Jr. et al.
2020/0113420 A1 4/2020 Sato et al.
2020/0352598 A1 11/2020 Elmouelhi et al.

\* cited by examiner

SHEATH STEPWISE DILATION

RELATED APPLICATION

This application is a continuation application of U.S. patent application Ser. No. 17/858,349 filed Jul. 6, 2022 which is a continuation application of U.S. patent application Ser. No. 17/524,260 filed Nov. 11, 2021, now U.S. Pat. No. 11,439,800, issued on Sep. 13, 2022, which claims priority to U.S. Provisional Patent Application No. 63/113,921 filed on Nov. 15, 2020. The entire contents of each of these applications are incorporated herein by reference.

TECHNICAL FIELD

This disclosure generally relates to sheaths, sheath assemblies, and related systems and methods. Certain such embodiments are described herein in the context of medical percutaneous interventional and diagnostic procedures as exemplary types of applications in which the sheaths, sheath assemblies, and related systems and methods can be used, for instance, to facilitate catheter or other device introduction through a vessel to a region of interest.

BACKGROUND

Medical diagnostic and interventional procedures are performed to assess, and when necessary take action to address, one or more conditions at a variety of anatomical locations. In many such procedures, an intravascular device, such as a catheter sheath, is inserted into a patient's vessel (e.g., artery) at an access site on the patient and traversed through the vessel to the particular region of interest.

In one such example where the cardiac region is the region of interest, medical diagnostic and interventional procedures commonly require two separate access sites on the patient. Generally, such procedures use one access site at the Femoral Artery and another, separate access site at the Radial Artery, the Contralateral Femoral Artery, or other similarly sized vessels (e.g., Subclavian Artery). These separate access sites are then used to insert the necessary diagnostic instrument(s) and interventional instrument(s) into the patient and separately guide these instruments to the cardiac region of interest. Because such procedures commonly utilize multiple instruments at the cardiac region of interest, the separate access sites at the patient can allow for the capacity needed (e.g., via both of the Femoral and Radial Arteries) to traverse the instrument payloads to the cardiac region of interest.

Moreover, regardless of which specific access sites on the patient are utilized, gaining access to the arterial, or in some cases venous, vascularization can be challenging and add additional complications to an already challenging percutaneous procedure. Factors contributing to the difficulty of access can include the muscular layer of the vessel contracting as a result of puncture of the vessel, the thickness of the vessel wall and its tendency to roll inwards towards the vessel lumen when placed under pressure, the possible interference of a large fascia layer prior to reaching the vessel itself, and the slipperiness of the vessel which makes the vessel an unsteady and unanchored target. Over the years, percutaneous interventionalist have inserted catheters into the vasculature using a Seldinger technique. This method works well when introducing devices that are perfectly axisymmetric and include smooth, gradual, axisymmetric transition surfaces without any steep step-ups in diameter as the device enters the vasculature. As a result, most endovascular devices have been designed to be axisymmetric with smooth, gradual, axisymmetric transition surfaces. However, in instances where a non-axisymmetric (e.g., asymmetric) device is to be inserted into the vasculature, the noted factors contributing to the difficulty of access can impede non-axisymmetric device access to the vascularization.

SUMMARY

While prior techniques have been learned to introduce axisymmetric devices into the vasculature, there is a need for features that can facilitate efficient non-axisymmetric device access to the arterial, or in some cases venous, vascularization. For example, certain procedures may require additional device capacity, and thus the ability to deliver multiple device(s), and, thereby, can benefit from the use of multiple catheters, or a multi-lumen asymmetric catheter, at a single access site to increase the delivery capacity, or payload, possible via the single access site. The present disclosure describes various features for facilitating efficient non-axisymmetric (e.g., asymmetric) device access to the vascularization of a patient via a single access site. Examples include a sheath assembly with at least two sheaths, spaced apart (e.g., radially spaced apart in a generally "stacked" configuration) from one another, and a sequence of two or more step-up dilations, spaced longitudinally apart, along the length of the sheath assembly where the cross-sectional diameter of the sheath assembly increases in a distal-to-proximal direction.

In general, various embodiments relating to sheaths, sheath assemblies, add-on sheath kits, and related systems and methods are disclosed herein. In particular, embodiments disclosed herein can facilitate medical diagnostic and interventional procedures via a single access site at the patient using a non-axisymmetric (e.g., asymmetric) sheath or sheath assembly. Thus, embodiments disclosed herein can facilitate a percutaneous medical interventional procedure using a single (e.g., Femoral Artery) access site at the patient, thereby reducing the number of access sites needed for such procedure by eliminating the need for a second access site (e.g., eliminating the need for a Radial Artery access site) and, in turn, eliminating risks associated with a second access site and reducing overall procedure time. As a result, embodiments disclosed herein can allow for less invasive procedures and preserve the second access site for any future procedures. At the same time, embodiments disclosed herein can provide these advantages while facilitating efficient non-axisymmetric (e.g., asymmetric) sheath access, and thus the ability to deliver additional payload capacity, to the vascularization of a patient via a single access site and still maintaining the functionality that would ordinarily be provided via a second access site.

One embodiment includes a sheath assembly. This sheath assembly embodiment includes a first sheath, a second sheath, and an attachment mechanism. The first sheath includes a first sheath first end portion, a first sheath second end portion opposite the first sheath first end portion, a first sheath inner surface, and a first sheath outer surface opposite the first sheath inner surface. The first sheath inner surface defines a first sheath lumen extending along a first sheath central longitudinal axis between the first sheath first end portion and the first sheath second end portion. The second sheath includes a second sheath first end portion, a second sheath second end portion opposite the second sheath first end portion, a second sheath inner surface, and a second sheath outer surface opposite the second sheath inner surface. The second sheath inner surface defines a second sheath lumen extending along a second sheath longitudinal axis between the second sheath first end portion and the second sheath second end portion. The attachment mechanism couples the second sheath to the first sheath. The attachment mechanism includes an attachment mechanism step-up dilation. At least a portion of the attachment mechanism is asymmetrical, at the attachment mechanism step-up dilation, about the first sheath central longitudinal axis.

In a further embodiment of the sheath assembly, the attachment mechanism step-up dilation is located between the first sheath second end portion and the second sheath second end portion.

In a further embodiment of the sheath assembly, the attachment mechanism step-up dilation includes a first attachment mechanism step-up dilation at a first attachment mechanism portion and a second attachment mechanism step-up dilation at a second attachment mechanism portion, with the second attachment mechanism step-up dilation being different than the first attachment mechanism step-up dilation. The attachment mechanism includes a first longitudinal cross-sectional profile, at the first attachment mechanism portion, that is asymmetrical about the first sheath central longitudinal axis, and the attachment mechanism includes a second longitudinal cross-sectional profile, at the second attachment mechanism portion, that is symmetrical about the first sheath central longitudinal axis. In one such example, the first attachment mechanism portion and the second attachment mechanism portion can be included at a common longitudinal location on the attachment mechanism. The first attachment mechanism portion can interface with the second sheath outer surface, and the second attachment mechanism portion can be opposite the second sheath. The first attachment mechanism step-up dilation can have a first slope that is defined by a first attachment mechanism step-up dilation longitudinal length and a first attachment mechanism step-up dilation radial height, and the second attachment mechanism step-up dilation can have a second slope that is defined by a second attachment mechanism step-up dilation longitudinal length and a second attachment mechanism step-up dilation radial height, and where the second slope is different than the first slope. For instance, the first attachment mechanism step-up dilation radial height can be at a side of the attachment mechanism facing the second sheath and the second attachment mechanism step-up dilation radial height can be at another side of the attachment mechanism opposite the second sheath, and where the first attachment mechanism step-up dilation radial height is greater than the second attachment mechanism step-up dilation radial height. The first slope of the first attachment mechanism step-up dilation can be greatest at a location proximate a distal-most interface between the attachment mechanism and the first sheath, and the first slope of the first attachment mechanism step-up dilation can decrease in a direction moving proximally toward the second sheath. For instance, the first slope of the first attachment mechanism step-up dilation can include a first slope region and a second slope region, where the first slope region has a greater slope magnitude than the second slope region, where the first slope region is distal of the second slope region, and where the first slope region extends a portion of the first attachment mechanism step-up dilation longitudinal length from the distal-most interface between the attachment mechanism and the first sheath to the second slope region. The first attachment mechanism step-up dilation radial height can be greater than the first attachment mechanism step-up dilation longitudinal length. In some examples, the first attachment mechanism step-up dilation radial height is between 0.254 to 1.27 cm, and the first attachment mechanism step-up dilation longitudinal length is between 0.254 to 0.635 cm.

In a further embodiment of the sheath assembly, the attachment mechanism includes a non-dilation region defining a portion of the attachment mechanism along which a cross-sectional diameter of the attachment mechanism is constant, and the non-dilation region of the attachment mechanism is located longitudinally between the first attachment mechanism step-up dilation and a distal-most end of the second sheath. The non-dilation region can extend along a non-dilation region longitudinal length from a proximal end of the first attachment mechanism step-up dilation to the distal-most end of the second sheath, and the non-dilation region longitudinal length can be at least 5 cm. The second sheath can include a second sheath step-up dilation, and the second sheath step-up dilation can be included at a distal-most end of the second sheath interfacing with the non-dilation region of the attachment mechanism. For instance, the second sheath can include a first distal wall portion forming a first portion of an opening of the second sheath lumen at a location adjacent the attachment mechanism, and the second sheath can include a second distal wall portion forming a second portion of the opening of the second sheath lumen at a location opposite the attachment mechanism, where the first distal wall portion is more distally located on the sheath assembly than the second distal wall portion. An angle, defined relative to the first sheath central longitudinal axis, can define a slope extending between the first distal wall portion and the second distal wall portion over a second sheath step-up dilation longitudinal length, and this angle can be between fifteen and seventy-five degrees.

In a further embodiment of the sheath assembly, the second sheath an be configured to transition between an expanded state and a collapsed state. The second sheath can be biased to the expanded state, and the second sheath can be configured such that the bias to the expanded state is overcome when the second sheath outer surface comes into contact with a vessel wall defining a vessel lumen thereby transitioning the second sheath to the collapsed state.

Various embodiments described herein, including the sheath assembly embodiment noted above, can provide a sheath that is configured to transition between an expanded state and a collapsed state. Such a sheath can allow for a reduced profile in the collapsed state, for instance, while the sheath is being traversed through a vessel, while also providing the ability to accommodate one or more instruments therein when in the expanded state, for instance once the sheath has reached the region of interest. This sheath can be configured to be added on to another sheath by securing the two sheaths to one another via one or more attachment mechanisms. In this way, the add-on sheath configured to transition between expanded and collapsed states can be used with another sheath already intended for use at one access site that has limited available space.

An additional embodiment includes a method of using a sheath assembly. This method embodiment includes the step of securing a second sheath to a first sheath via an attachment mechanism such that a first portion of a second sheath outer surface interfaces with a first sheath outer surface. The first sheath defines a first sheath central longitudinal axis, the attachment mechanism includes an attachment mechanism step-up dilation, and at least a portion of the attachment mechanism is asymmetrical, at the attachment mechanism step-up dilation, about the first sheath central longitudinal axis. This method embodiment also includes the steps of inserting a guidewire to a region of interest within a patient, and placing the first sheath over the guidewire and inserting the first sheath and the second sheath into the patient through a single access site at the patient. This method further includes the steps of contacting the single access site with the attachment mechanism step-up dilation and then with the second sheath, and transitioning the second sheath from an expanded state to a collapsed state upon inserting the second sheath into the patient, with the second sheath collapsing to the collapsed state in a direction toward the first sheath. And, this method embodiment includes the step of inserting an instrument through the second sheath and causing the second sheath to transition from the collapsed state to the expanded state.

In a further embodiment of the method, the method can additionally include the step of, after contacting the single access site with the attachment mechanism step-up dilation and before contacting the single access site with the second sheath, contacting the single access site with an attachment mechanism non-dilation region. The attachment mechanism non-dilation region can define a portion of the attachment mechanism along which a cross-sectional diameter of the attachment mechanism is constant.

The details of one or more examples are set forth in the accompanying drawings and the description below. Other features, objects, and advantages will be apparent from the description and drawings.

BRIEF DESCRIPTION OF THE DRAWINGS

The following drawings are illustrative of particular embodiments of the present invention and therefore do not limit the scope of the invention. The drawings are intended for use in conjunction with the explanations in the following description. Embodiments of the invention will hereinafter be described in conjunction with the appended drawings, wherein like numerals denote like elements. The drawings are not necessarily to scale, though certain embodiments can include one or more components at the scale shown.

DETAILED DESCRIPTION

The following detailed description is exemplary in nature and is not intended to limit the scope, applicability, or configuration of the invention in any way. Rather, the following description provides some practical illustrations for implementing embodiments of the present invention. Examples of constructions, materials, and/or dimensions are provided for selected elements. Those skilled in the art will recognize that many of the noted examples have a variety of suitable alternatives.

Figure 1:
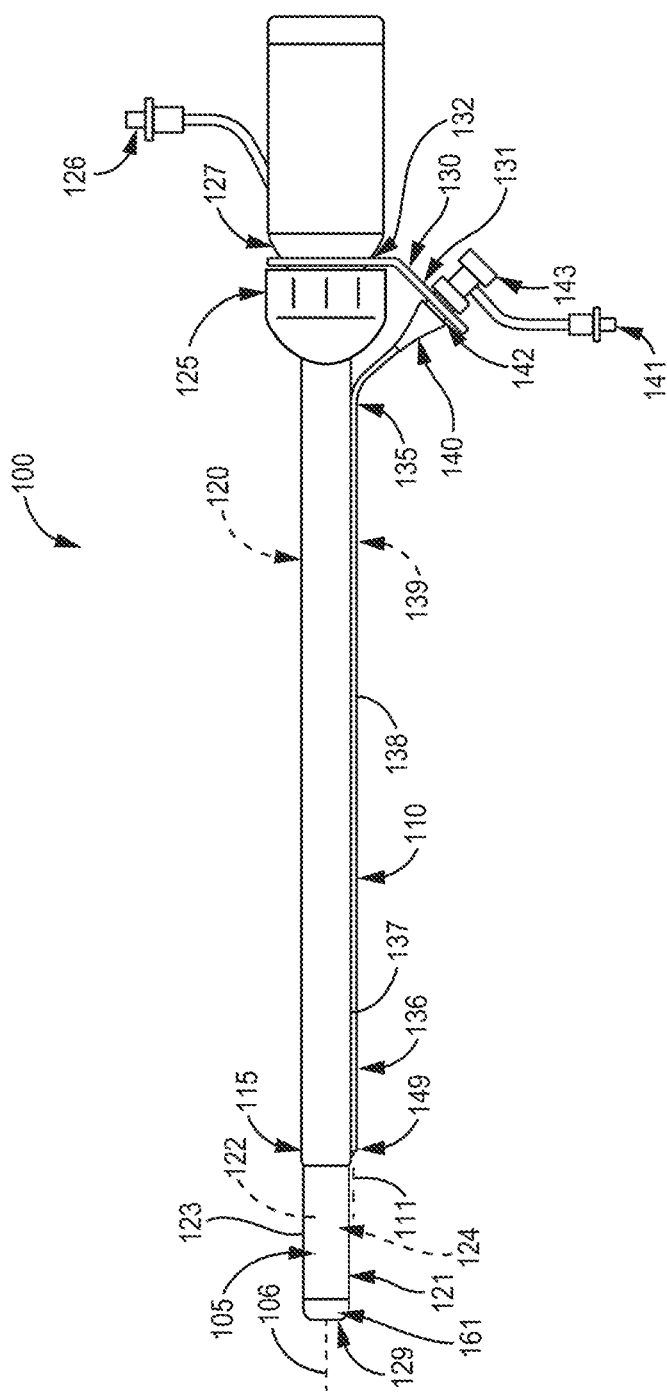
FIG. 1 is a side elevational view of an embodiment of a sheath assembly.

FIG. 1 shows a side elevational view of an exemplary embodiment of a sheath assembly 100. The sheath assembly 100 includes a first sheath 105 and a second sheath 110. As shown in this illustrated embodiment, the first sheath 105 and the second sheath 110 are secured together by an attachment mechanism 115 in a stacked arrangement such that the first sheath 105 and the second sheath 110 are arranged side-by-side with their respective outer surfaces interfacing with one another. As also shown in the illustrated embodiment, the attachment mechanism 115 extends over at least a portion of the outer surface of the first sheath 105. In this stacked arrangement, a first sheath central longitudinal axis 106, of the first sheath 105, is offset from and generally parallel to a second sheath central longitudinal axis 111, of the second sheath 110.

In the sheath assembly 100, the first sheath 105 includes a first sheath first end portion 120, a first sheath second end portion 121, a first sheath inner surface 122, and a first sheath outer surface 123. The first sheath second end portion 121 is opposite the first sheath first end portion 120. The first sheath outer surface 123 is opposite the first sheath inner surface 122. The first sheath inner surface 122 defines a first sheath lumen 124 extending along the first sheath longitudinal axis 106 between the first sheath first end portion 120 and the first sheath second end portion 121. The first sheath second end portion 121 can include a first sheath opening 129, for instance to allow an instrument and/or guide wire inserted within the first sheath lumen 124 to extend out from the first sheath 105 at the first sheath opening 129.

At the first sheath first end portion 120 is a proximal hub 125. The proximal hub 125 can be open to, and in communication with, the first sheath lumen 124. As such, the proximal hub 125 can be configured to facilitate access to the first sheath lumen 124. For example, the proximal hub 125 can be configured to receive one or more diagnostic or interventional instruments (e.g., a catheter) that are to be used for a procedure and delivered through the first sheath lumen 124. As shown here, the proximal hub 125 includes a flush port 126 and a clip attachment interface 127. The flush port 126 is configured to facilitate fluid communication with the first sheath lumen 124 and/or a diagnostic and/or interventional instrument within the first sheath lumen 124. The clip attachment interface 127 is configured to receive a clip 130 for securing proximal end portions of the sheaths 105, 110.

Also in the sheath assembly 100, the second sheath 110 includes a second sheath first end portion 135, a second sheath second end portion 136, a second sheath inner surface 137, and a second sheath outer surface 138. The second sheath second end portion 136 is opposite the second sheath first end portion 135. The second sheath outer surface 138 is opposite the second sheath inner surface 137. The second sheath inner surface 137 defines a second sheath lumen 139 extending along the second sheath central longitudinal axis 111 between the second sheath first end portion 135 and the second sheath second end portion 136. The second sheath second end portion 136 can include a second sheath opening 149, for instance to allow an instrument and/or guide wire inserted within the second sheath lumen 139 to extend out from the second sheath 110 at the second sheath opening 149. As shown in FIG. 1, the first sheath 105 and the second sheath 110 can be of a substantially similar length between their respective end portions 120, 135 and 121, 136. In particular, the first sheath first end portion 120 and the second sheath first end portion 135 can terminate at a similar proximal location, and the first sheath second end portion 121 and the second sheath second end portion 136 can terminate at a similar distal location (e.g., in FIG. 1, the second sheath second end portion 136 terminates slightly short, or slightly proximal, of the first sheath second end portion 121 (e.g., 1-10 cm, such as 3-6 cm, short of the first sheath second end portion 121)).

At the second sheath first end portion 135 is a proximal hub 140. The proximal hub 140 can be open to, and in communication with, the second sheath lumen 139 As such, the proximal hub 140 can be configured to facilitate access to the second sheath lumen 139. For example, the proximal hub 140 can be configured to receive one or more diagnostic or interventional instruments (e.g., a catheter) that are to be used for a procedure and delivered through the second sheath lumen 139. As shown here, the proximal hub 140 includes a flush port 141, a clip attachment interface 142, and an instrument insertion port 143. The flush port 141 is spaced apart from the instrument insertion port 143 and in communication with the second sheath lumen 139. As such, the flush port 141 is configured to facilitate fluid communication with the second sheath lumen 139 and/or a diagnostic and/or interventional instrument within the second sheath lumen 139. The clip attachment interface 142 is configured to receive the clip 130 for securing proximal end portions of the sheaths 105, 110. As shown in the illustrated embodiment, the clip attachment interface 142 includes a recessed slot formed at the proximal hub 140 and configured to create an interference fit with the clip 130, though in other embodiments the clip attachment interface 142 can include other types of structures configured to receive the clip 130. The instrument insertion port 143 is in communication with the second sheath lumen 139, and the instrument insertion port 143 is configured to receive a diagnostic and/or interventional instrument (e.g., a guidewire and a catheter) thereat and pass this instrument into the second sheath lumen 139.

The clip 130 is configured to secure the second sheath 110 to the first sheath 105. Specifically, the clip 130 is configured to secure the hub 125 to the hub 140. The clip 130 can include a first clip securement portion 131 configured to receive the second sheath 110 and a second clip securement portion 132, spaced apart from the first clip securement portion 131, configured to receive the first sheath 105. The clip attachment interface 142 is configured to receive the first clip securement portion 131 and the clip attachment interface 127 is configured to receive the second clip securement portion 132 so as to secure the proximal hub 140 to the proximal hub 125. In the illustrated embodiment, the first clip securement portion 131 is non-parallel to the second clip securement portion 132, with the first clip securement portion 131 extending at an angle between fifteen and eighty five degrees (e.g., between twenty five and seventy five degrees, between forty and sixty degrees) from a plane on which the second clip securement portion 132 lies. Each clip securement portion 131, 132 can include an aperture that secures around at least a portion of (e.g., all of) each respective clip attachment interface 142, 127.

Figure 2:
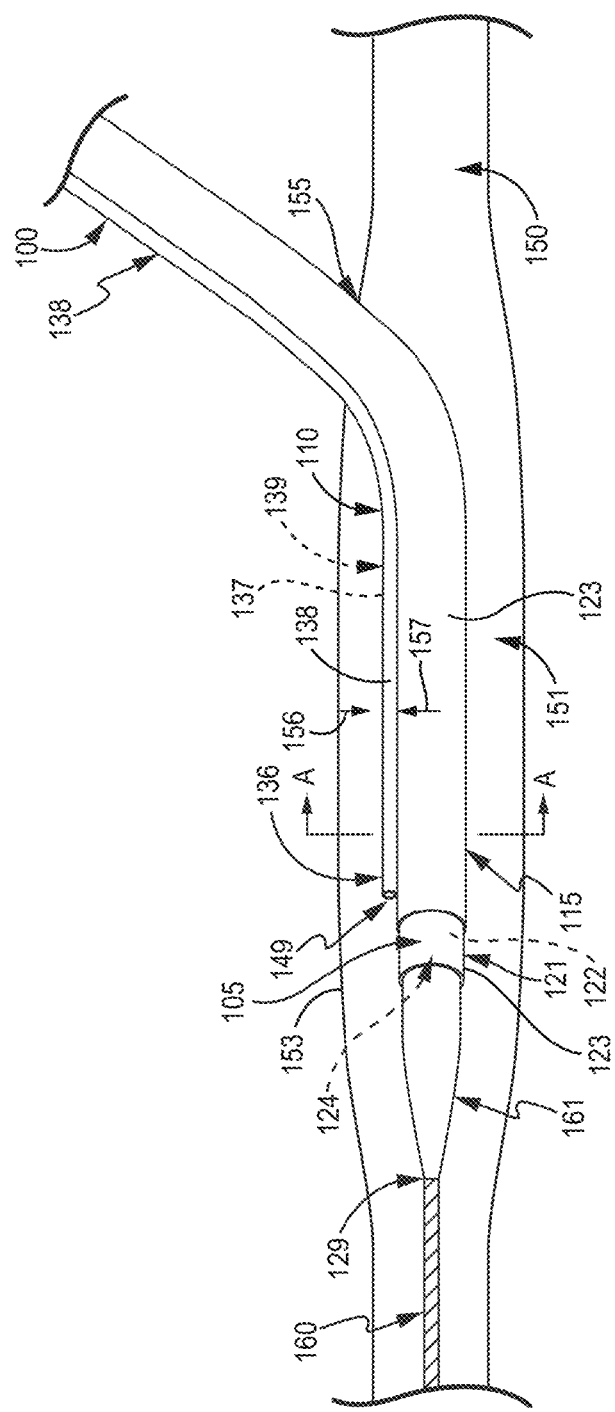
FIG. 2 is a side elevational view of a portion of the sheath assembly embodiment of FIG. 1 being inserted into a vessel lumen.
Figure 3:
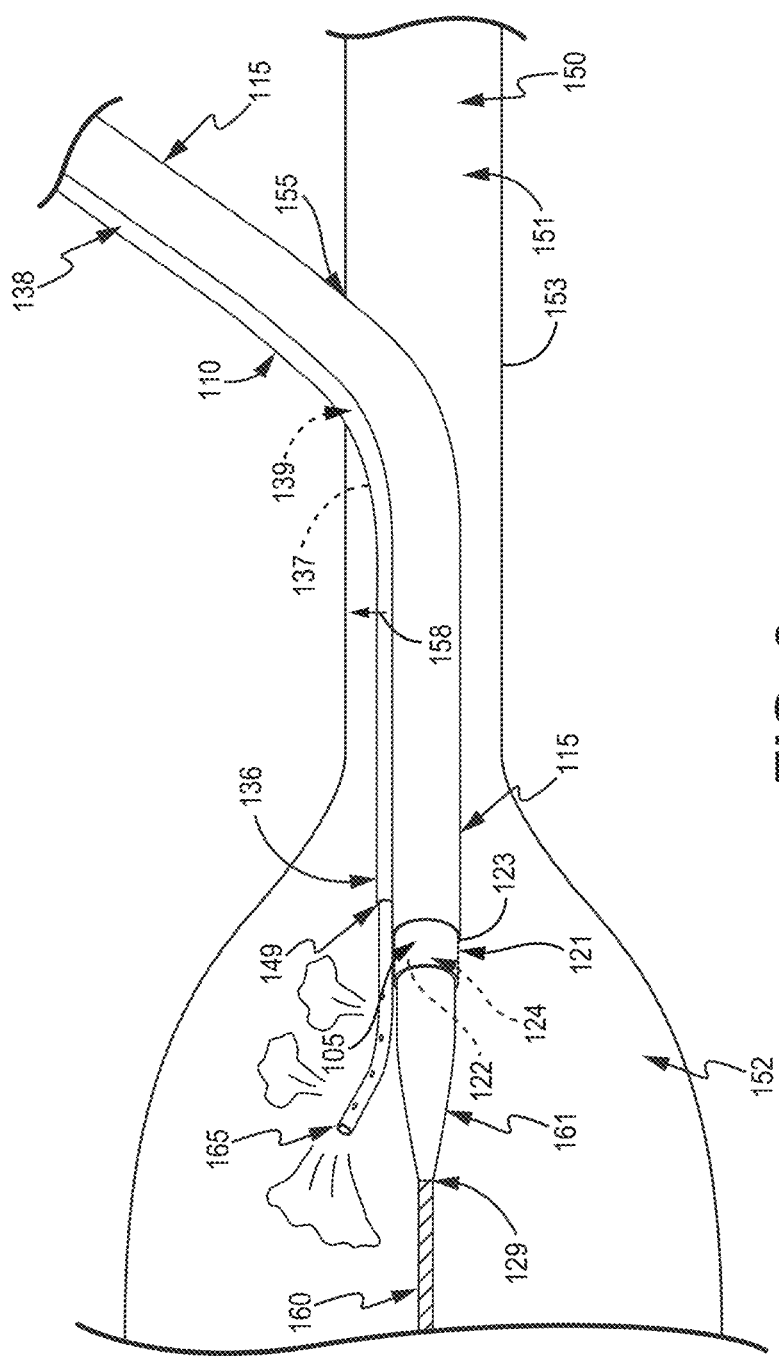
FIG. 3 is a side elevational view of a portion of the sheath assembly embodiment of FIG. 1 at a region of interest in the vessel lumen.

FIGS. 2 and 3 show a portion of the sheath assembly 100 deployed within a vessel 150, such as a blood vessel (e.g., artery) of a patient. As shown here, the sheath assembly 100, with both the first sheath 105 and the second sheath 110, is inserted into the vessel 150 via a single access site 155. In one exemplary application, the vessel 150 can be the Femoral Artery and the sheath assembly 100 can be inserted into the Femoral Artery via the single access site 155. In this way, both the first sheath 105 and the second sheath 110 can facilitate a percutaneous diagnostic and/or interventional procedure using the single access site 155 and thereby eliminate risks and complications associated with a second access site for deploying one of the sheaths.

To facilitate deployment of the sheath assembly 100 via the single access site 155, the second sheath 110 can be configured to transition between an expanded state and a collapsed state. In this way, the second sheath 110 can allow the sheath assembly 100 to have a reduced profile, when the second sheath 110 is in the collapsed state, for instance, while the sheath assembly 100 is being inserted in, and traversed through, the vessel 150. And, in this way, the second sheath 110 can also provide the ability to accommodate one or more diagnostic and/or interventional instrument(s) (e.g., a diagnostic or auxiliary catheter) within the second sheath 110 when the second sheath 110 is in the expanded state, for instance once the sheath has reached a region of interest 152. FIG. 2 illustrates a side elevational view of the portion of the sheath assembly 100 being inserted into a vessel lumen 151 of the vessel 150 with the second sheath 110 in a generally collapsed state. FIG. 3 illustrates a side elevational view of the portion of the sheath assembly 100 having reached the region of interest 152 in the vessel lumen 151 and now with the second sheath 110 in a generally expanded state.

As shown, the sheath assembly 100 can be inserted within the vessel lumen 151 and traversed through the vessel 150 to the region of interest 152 using a guidewire 160. The first sheath 105 can be placed onto the guidewire 160 such that the guidewire 160 is received within the first sheath lumen 124. The sheath assembly 100 can then be advanced into the vessel lumen 151 through the single access site 155 over the guidewire 160 at the first sheath 105. In some embodiments, the first sheath 105 can include an introducer 161 at the first sheath second end portion 121 to assist in deploying the sheath assembly 100 into, and through, the vessel lumen 151.

As noted, the second sheath 110 can be configured to transition between an expanded state and a collapsed state. In the illustrated embodiment, the second sheath 110 can be biased to the expanded state, and the second sheath 110 can be configured to transition from the expanded state to the collapsed state when the second sheath outer surface 138 comes into contact with a vessel wall 153 defining, for instance, the single access site 155 and the vessel lumen 151. In this way, the second sheath 110 can be configured such that the bias to the expanded state is overcome when the second sheath outer surface 138 comes into contact with the vessel wall 153. Therefore, in such embodiments, when the sheath assembly 100 is being inserted within and traversed through the vessel lumen 151, as in FIG. 2, the second sheath 110 can generally be in contact with the vessel wall 153 and thus be in a collapsed state. Also, in such embodiments, the sheath assembly 100 can be configured such that the second sheath 110 is configured to transition from the expanded state to the collapsed state, and be maintained in the collapsed state, while the first sheath 105 is maintained in a first sheath expanded state. This can maintain the first sheath lumen 124 at its designed capacity, for example, so as to be useful in instances where the first sheath 105 receives the guidewire 160 for advancing the sheath assembly 110 to the region of interest 152. In some cases, the first sheath 105 may not be collapsible, though certain embodiments can include a first sheath that is configured to transition between collapsed and expanded states.

The second sheath 110 can include one or more features to facilitate transitioning between expanded and collapsed states. For example, the first sheath 105 can have a first hardness, X, and the second sheath 110 can have a second hardness, Y, where the first hardness, X, of the first sheath 105 is greater than the second hardness, Y, of the second sheath 110. As examples, the first sheath 105 can have a Rockwell hardness between 70 A and 100 A, such as between 80 A and 90 A, and the second sheath 110 can have a Rockwell hardness between 30 A and 70 A, such as between 40 A and 60 A. In this way, the second sheath 110 can be configured to be collapsible upon the forces imparted on the second sheath 110 by each of the harder first sheath 105 and the vessel wall 153. More specifically, as the second sheath 110 comes into contact with the vessel wall 153, the vessel wall 153 can impart a force 156 in a first direction on the second sheath outer surface 138 while the harder first sheath 105 can impart a force 157 in a second, opposite direction on the second sheath outer surface 138 causing the second sheath to collapse between the first force 156 and the second force 157. In this case, the second sheath 110 will collapse in a direction toward the first sheath 105. Accordingly, the second sheath 110 is able to transition from the expanded state to the collapsed state and thereby render the sheath assembly 100 more compact within the vessel lumen 151.

As noted, the second sheath 110 can have one or more dimensions and/or include one or more materials (e.g., that contribute to the hardness or stiffness of the second sheath 110) that allow it to collapse when being inserted into, and traversed through, the vessel lumen 151. For example, the second sheath 110 can include a wall thickness, defined between the second sheath outer surface 138 and the second sheath inner surface 137, that is less than a wall thickness of the first sheath 105, defined between the first sheath outer surface 123 and the first sheath inner surface 122. As one example, the wall thickness of the second sheath can be between 0.1 mm and 1.5 mm, such as between 0.15 mm and 0.75 mm (e.g., between 0.15 mm and 0.5 mm) or between 0.25 mm and 0.5 mm. As another example, the second sheath 110 can be made of a collapsible polymer or mesh material that is configured to collapse under forces exerted on it by the vessel wall 153 (e.g., a vessel wall of the Femoral Artery). For instance, the second sheath 110 can include biocompatible polyurethane (e.g., Pellethane™). Depending on the particular application, the combination of material including biocompatible polyurethane along with the hardness and/or wall thickness of the second sheath 110 relative to the first sheath 105 can allow the second sheath 110 to transition from the expanded state to the collapsed state when inserted into, and traversed through, the vessel lumen 151 as a result of contact with the vessel wall 153.

To allow the second sheath 110 to collapse to its fullest extent, no hardware (e.g., instrument, guidewire, etc.) may be present within the second sheath lumen 139 when the sheath assembly 100 is inserted into and traversed through the vessel lumen 151, as in FIG. 2. Then, once the sheath assembly 100 has reached the region of interest 152, as in FIG. 3, one or more hardware components (e.g., a guidewire, and/or a diagnostic and/or interventional instrument, such as a diagnostic or auxiliary catheter) can be inserted within the second sheath lumen 139.

The second sheath 110 can be configured to transition from the collapsed state, as in FIG. 2 when the second sheath 110 is in contact with the vessel wall 153, toward the expanded state, as in FIG. 3, upon insertion of a hardware component (e.g., a rigid hardware component) within the second sheath lumen 139. FIG. 3 shows a catheter 165 (e.g., a pigtail catheter) inserted within the second sheath lumen 139 and extending out from the second sheath opening 149 at the region of interest 152. Inserting the hardware component, such as the catheter 165, within the second sheath lumen 139 can impart a force 158 in the second direction on the second sheath 110 causing the second sheath 110 to expand out from the collapsed state. Thus, this force 158 imparted by the catheter 165 on the second sheath 110 in the second direction can counteract some, or all, of the force 156 applied by the vessel wall 153 allowing the second sheath 110 to transition from the collapsed state, as in FIG. 2 when the second sheath 110 is in contact with the vessel wall 153, toward, or to, the expanded state, as in FIG. 3.

Depending on the particular application, such as the hardware inserted within the second sheath lumen 139, the second sheath 110 may only partially transition from the collapsed state to the expanded state (e.g., the second sheath 110 extends out from the first sheath 105 to a lesser extent than when the sheath assembly 100 is not within the vessel 150) when a hardware component is present within the second sheath lumen 139, as in FIG. 3. Because the second sheath 110 can be configured to collapse when in contact with the vessel wall 153, the force 156 applied by the vessel wall 153 can continue to counteract the force 158 and thereby constrain the expansion of the second sheath 110 when the hardware component, such as the catheter 165, is present within the second sheath lumen 139. Accordingly, the second sheath 110 can be configured to transition from the collapsed state toward the expanded state only to the extent needed to accommodate the hardware component within the second sheath lumen 139, thereby keeping a minimum necessary profile of the sheath assembly 100 even when the second sheath 110 is actively being used during a procedure. In this way, the second sheath 110, configured to transition between expanded and collapsed states, can facilitate a reduced profile of the sheath assembly 100 both during insertion and placement as well as during usage of the second sheath 110 during a procedure. As a result, the sheath assembly 100 can be capable of use via the single access site 155.

Additional details relating to the second sheath 110 being configured to transition between collapsed and expanded states can be found in U.S. patent application Ser. No. 16/871,299, the entire contents of which are hereby incorporated by reference.

Figure 4:
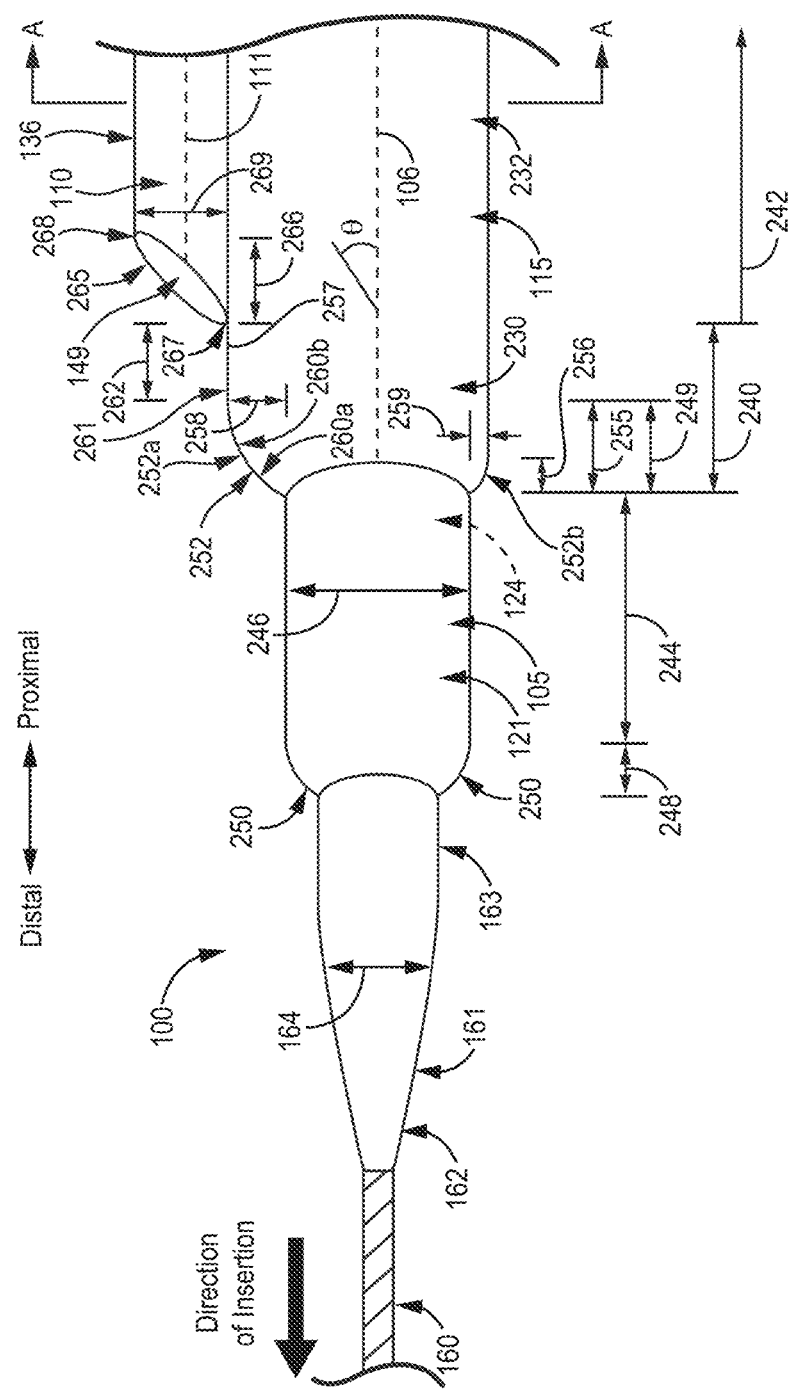
FIG. 4 is a close-up, side elevational view of a portion of the sheath assembly of FIG. 1 illustrating exemplary step-wise dilation features.
Figure 5:
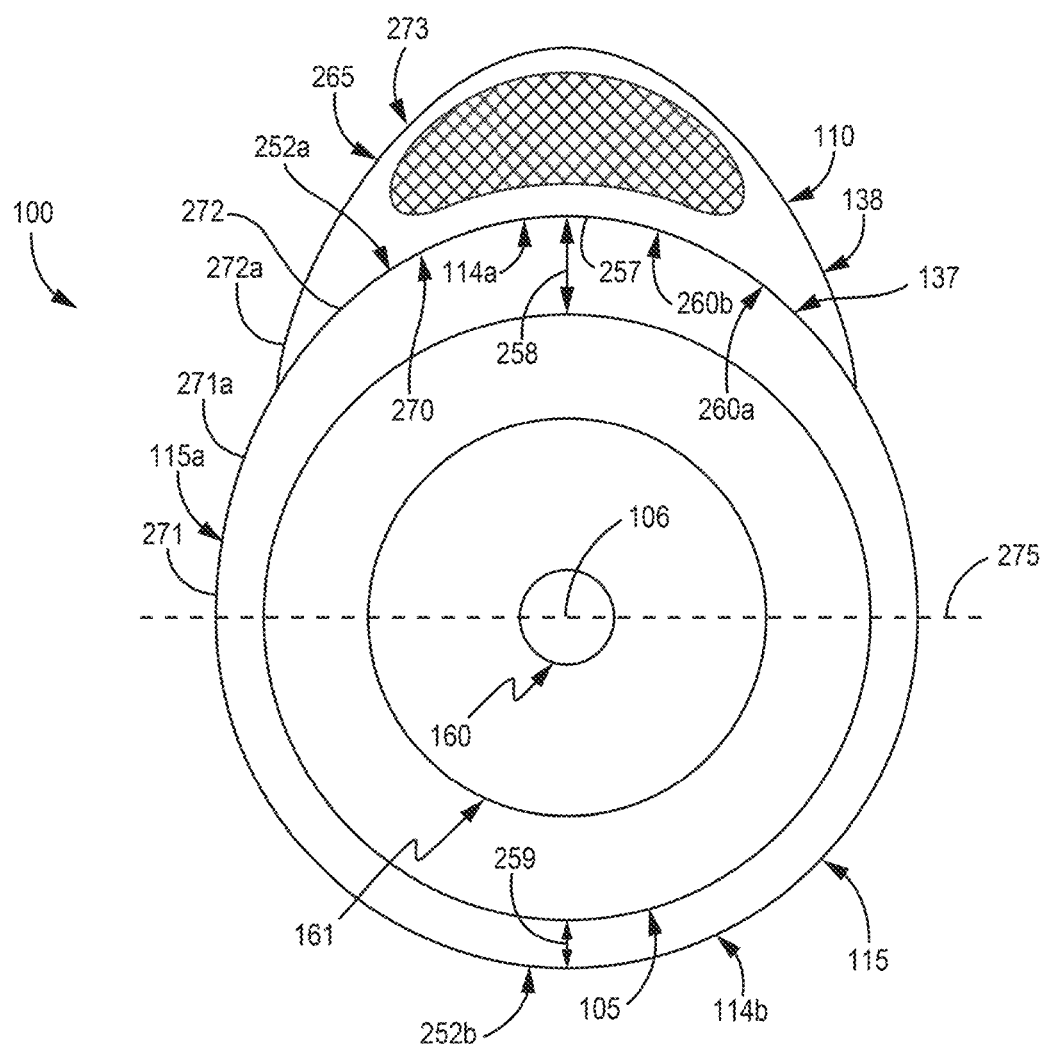
FIG. 5 is a cross-sectional view, taken along line A-A in FIG. 4, of the sheath assembly of FIG. 1 with the second sheath of the sheath assembly in an expanded state.

To also facilitate deployment of the sheath assembly 100 via the single access site 155, the sheath assembly 100 can include one or more features, some or all of which can be referred to as stepwise dilation features, to facilitate efficient insertion of the sheath assembly 100 into the vessel 150 via the single access site 155. FIGS. 4 and 5 show a portion of the sheath assembly 100 with exemplary features that can be useful in facilitating efficient insertion of the sheath assembly 100 into the vessel 150 via the single access site 155. Specifically, FIG. 4 is a close-up, side elevational view of a portion of the sheath assembly 100 illustrating such exemplary features, and FIG. 5 is a cross-sectional view, taken along line A-A in FIG. 4, of the sheath assembly 100 with such exemplary features and with the second sheath 110 in an expanded state.

As illustrated at FIGS. 4 and 5, the sheath assembly 100 can be a non-axisymmetric (e.g., asymmetric) device. For example, as best seen in FIG. 5, the sheath assembly 100 is configured to be asymmetrical about a central longitudinal axis of the sheath assembly 100. More specifically, in the illustrated embodiment, the sheath assembly 100 is configured to be asymmetrical about the guidewire 160 received at the first sheath lumen 124, and, thus, asymmetrical about the first sheath longitudinal axis 106.

As shown in the illustrated embodiment, the sheath assembly 100 can include one or more profile step-up dilations included at the introducer 161, the first sheath 105, the second sheath 110, the attachment mechanism 115 (as noted and illustrated, the attachment mechanism 115 can be positioned over, and around, at least a portion of the first sheath 105), and/or the second sheath 110. In particular, in some embodiments, the sheath assembly 100 can include two or more step-wise up-dilation increases in the longitudinal cross-sectional diameter sequentially moving in a direction from a distal end toward a proximal end of the sheath assembly 100. Thus, the one or more profile step-up dilations can act to increase the profile (e.g., longitudinal cross-sectional diameter) of the sheath assembly 100 moving in a distal-to-proximal direction along the sheath assembly 100.

In the illustrated embodiment, a portion of the sheath assembly 100 can be symmetrical about the first sheath longitudinal axis 106 and another portion of the sheath assembly 100 can be asymmetrical about the first sheath longitudinal axis 106. Specifically, in the illustrated embodiment, the sheath assembly 100 is symmetrical about the first sheath longitudinal axis 106 from the distal end of the sheath assembly 100 (e.g., the distal end of the introducer 161) moving proximally to the distal-most location where the attachment mechanism 115 is present (e.g., and where the attachment mechanism 115 interfaces with the first sheath 105). And in the illustrated embodiment, at the distal-most location where the attachment mechanism 115 is present (e.g., and where the attachment mechanism 115 interfaces with the first sheath 105), the sheath assembly 100 becomes asymmetrical about the first sheath longitudinal axis 106. More specifically, in the illustrated embodiment, the sheath assembly 100 can have a first asymmetrical configuration 230 about the first sheath longitudinal axis 106 for a longitudinal length 240 along the sheath assembly 100 from the distal-most location where the attachment mechanism 115 is present (e.g., and where the attachment mechanism 115 interfaces with the first sheath 105) to the distal-most location where the second sheath 110 is present (e.g., and where the second sheath 110 interfaces with the attachment mechanism 115). And, the sheath assembly 100 can have a second asymmetrical configuration 232, different than the first asymmetrical configuration 230, about the first sheath longitudinal axis 106 for a longitudinal length 242 along the sheath assembly 100 from the distal-most location where the second sheath 110 is present (e.g., and where the second sheath 110 interfaces with the attachment mechanism 115) to a location where the second sheath 110 terminates (e.g., to the second sheath first end portion 135).

These one or more profile step-up dilations can be sequenced and configured to reduce difficulties associated with inserting a non-axisymmetric device into the vasculature via the single access site. For example, these one or more profile step-up dilations can help to reduce the immediacy of the transition from the relatively smaller cross-section diameter of the guidewire 160 (e.g., 0.0762 cm to 0.1016 cm) to the relatively larger cross-sectional diameter of the sheath assembly 100 where the second sheath 110 is located (e.g., 0.508 cm to 0.889 cm, such as when the second sheath 110 is in the collapsed state or larger when the second sheath is in the expanded state).

As shown, the introducer 161 (sometimes referred to as a "dilator") can be present at a distal end of the sheath assembly 100. Once the guidewire 160 is placed into the target vasculature, the sheath assembly 100 can be delivered over the guidewire 160. The introducer 161 can be configured to be the first component of the sheath assembly 100 to encounter the single access site 155. As shown in the illustrated embodiment, the introducer 161 can have an introducer distal end portion 162 and an introducer proximal end portion 163. The introducer 161 can have a smallest cross-sectional diameter (e.g., longitudinal cross-sectional diameter 164) at the introducer distal end portion 162 and a largest cross-sectional diameter (e.g., longitudinal cross-sectional diameter 164) at the introducer proximal end portion 163. The sheath assembly 100 can be axisymmetric about the central longitudinal axis of the introducer 161. In some examples, such as that shown here, the introducer 161 can increase in cross-sectional diameter from the introducer distal end portion 162 to the introducer proximal end portion 163 at a constant rate. In such examples, the introducer 161 can be, for instance, generally conical in shape with the tip of the conical shape at the introducer distal end portion 162 and the base of the conical shape at the introducer proximal end portion 163. As the introducer 161 is introduced into the vessel, this increase in the cross-sectional diameter of the introducer 161 in the distal-to-proximal direction can be configured to gradually stretch the vessel at the single access site 155 from the profile of the guidewire 160 to the profile of the first sheath 105.

Moving proximally from the introducer 161, the first sheath 105 can increase the profile of the sheath assembly 100 from that of the introducer 161. The first sheath 105 can be configured to be the next component, after the introducer 161, of the sheath assembly 100 to encounter the single access site 155 as the sheath assembly 100 continues to be introduced into the vessel. As shown in the illustrated embodiment, the first sheath second end portion 121 can define the first sheath distal end portion. The first sheath 105 can include a first sheath step-up dilation 250, at the first sheath second end portion 121, and the first sheath step-up dilation 250 can be configured to increase a cross-sectional diameter (e.g., longitudinal cross-sectional diameter 246) along a first sheath step-up dilation longitudinal length 248 moving in a proximal direction. In particular, the first sheath 105 can have a smallest cross-sectional diameter (e.g., longitudinal cross-sectional diameter 246) at the distal-most end of the first sheath 105 where the first sheath 105 interfaces with the introducer 161, and the first sheath step-up dilation 250 can extend, along the first sheath step-up dilation longitudinal length 248, from this smallest cross-sectional diameter (e.g., longitudinal cross-sectional diameter 246) at the distal-most end of the first sheath 105 where the first sheath 105 interfaces with the introducer 161 along the first sheath step-up dilation longitudinal length 248 in a proximal direction toward the attachment mechanism 115.

Where the first sheath step-up dilation 250 ends, and thus where first sheath step-up dilation longitudinal length 248 ends, the first sheath 105 can extend a longitudinal length 244 from the end of the first sheath step-up dilation 250 to the interface with the attachment mechanism 115. This longitudinal length 244 can be sufficiently long enough to allow the vessel, at the single access site 155, enough time during the sheath assembly 100 introduction, to relax and settle, uncurl any folds that may have formed at the vessel wall during introduction of the first sheath step-up dilation 250 at the single access site 155, and bounce back to the initial shape experienced at the outset of sheath assembly 100 introduction. In various embodiments, the longitudinal length 244 can be at least 5 cm, at least 8 cm, at least 10 cm, at least 12 cm, at least 15 cm, at least 20 cm, at least 25 cm, or at least 30 cm.

The first sheath step-up dilation 250 can be configured to transition the first sheath 105 from its smallest cross-sectional diameter (e.g., longitudinal cross-sectional diameter 246) at the distal-most end of the first sheath 105 to its largest cross-sectional diameter (longitudinal cross-sectional diameter 246) at a more proximal location along the first sheath 105. Thus, the first sheath step-up dilation 250 can begin at a distal-most interface of the first sheath 105 and the introducer 161. In the illustrated embodiment, the first sheath step-up dilation 250 can be axisymmetric about the first sheath longitudinal axis 106, and the first sheath 105 itself can be axisymmetric about the first sheath longitudinal axis 106.

Moving proximally from the first sheath 105, the attachment mechanism 115 can further increase the profile of the sheath assembly 100 from that of the first sheath 105. The attachment mechanism 115 can be configured to be the next component, after the first sheath 105, of the sheath assembly 100 to encounter the single access site 155 as the sheath assembly 100 continues to be introduced into the vessel. The attachment mechanism 115 can include an attachment mechanism step-up dilation 252 beginning at a distal-most longitudinal location where the attachment mechanism 115 interfaces with the first sheath 105. The attachment mechanism step-up dilation 252 can be configured to increase a cross-sectional diameter (e.g., longitudinal cross-sectional diameter 246) along an attachment mechanism step-up dilation longitudinal length 249 moving proximally from the distal-most longitudinal location where the attachment mechanism 115 interfaces with the first sheath 105. In particular, the attachment mechanism 115 can have a smallest cross-sectional diameter (e.g., longitudinal cross-sectional diameter 246) at the distal-most end of the attachment mechanism 115 where the attachment mechanism 115 interfaces with the first sheath 105, and the attachment mechanism step-up dilation 252 can extend, along the attachment mechanism step-up dilation longitudinal length 249, from this smallest cross-sectional diameter (e.g., longitudinal cross-sectional diameter 246) at the distal-most end of the attachment mechanism 115 where the attachment mechanism 115 interfaces with the first sheath 105 along the attachment mechanism step-up dilation longitudinal length 249 in a proximal direction toward the second sheath 110.

As noted, and as shown in the illustrated embodiment, at the attachment mechanism 115, the sheath assembly 100 can transition from the axisymmetric configuration distal to the attachment mechanism 115 to the first asymmetrical configuration 230 (e.g., about the first sheath longitudinal axis 106) present at the attachment mechanism 115. In particular, the attachment mechanism step-up dilation 252 can be configured to transition the sheath assembly 100 from the axisymmetric configuration distal to the attachment mechanism 115 to the first asymmetrical configuration 230 (e.g., about the first sheath central longitudinal axis 106) present at the attachment mechanism 115.

To do so, the attachment mechanism step-up dilation 252 can be asymmetrical about the first sheath longitudinal axis 106. For example, the attachment mechanism step-up dilation 252 can include a first attachment mechanism step-up dilation 252a and a second attachment mechanism step-up dilation 252b that is different than the first attachment mechanism step-up dilation 252a. As such, for instance as seen at FIG. 5, the first attachment mechanism step-up dilation 252a can define a longitudinal cross-sectional profile of the attachment mechanism 115 that includes a first attachment mechanism portion 114a that is asymmetrical about the first sheath 105 (e.g., asymmetrical about the first sheath central longitudinal axis 106), and the second attachment mechanism step-up dilation 252b can define a longitudinal cross-sectional profile of the attachment mechanism 115 that includes a second attachment mechanism portion 114b that is symmetrical about the first sheath 105 (e.g., symmetrical about the first sheath central longitudinal axis 106). The first attachment mechanism step-up dilation 252a, and the first attachment mechanism portion 114a, can be present at a second sheath facing side 257, and the second attachment mechanism step-up dilation 252b, and the second attachment mechanism portion 114b, can be present at one or more sides of the attachment mechanism 115 not facing the second sheath 110.

In the illustrated embodiment, the first attachment mechanism step-up dilation 252a can have a different slope than the second attachment mechanism step-up dilation 252b. For instance, the first attachment mechanism step-up dilation 252a can have a first attachment mechanism step-up dilation longitudinal length 255 (e.g., beginning at the distal-most interface of the attachment mechanism 115 at the first sheath 105) and a first attachment mechanism step-up dilation radial height 258 (e.g., extending out from the outer surface of the first sheath 105) defining a first slope of the first attachment mechanism step-up dilation 252a. And the second attachment mechanism step-up dilation 252b can have a second attachment mechanism step-up dilation longitudinal length 256 (e.g., beginning at the distal-most interface of the attachment mechanism 115 at the first sheath 105) and a second attachment mechanism step-up dilation radial height 259 (e.g., extending out from the outer surface of the first sheath 105) defining a second slope of the second attachment mechanism step-up dilation 252b. To create the different slopes at the first and second attachment mechanism step-up dilations 252a, 252b, the first attachment mechanism step-up dilation longitudinal length 255 can be different than the second attachment mechanism step-up dilation longitudinal length 256 and/or the first attachment mechanism step-up dilation radial height 258 can be different than the second attachment mechanism step-up dilation radial height 259. In the illustrated embodiment, both the first attachment mechanism step-up dilation longitudinal length 255 is different (e.g., greater) than the second attachment mechanism step-up dilation longitudinal length 256 and the first attachment mechanism step-up dilation radial height 258 is different (e.g., greater) than the second attachment mechanism step-up dilation radial height 259.

With respect to the first attachment mechanism step-up dilation 252a, for example, the first slope of the first attachment mechanism step-up dilation 252a can be greatest at a location proximate the distal-most interface with the first sheath 105 and decrease in a direction moving proximally toward the second sheath 110. For instance, the first slope of the first attachment mechanism step-up dilation 252a can include a first slope region 260a and a second, different slope region 260b. The first slope region 260a can be distal of the second slope region 260b and extend a portion of the first attachment mechanism step-up dilation longitudinal length 255 from the distal-most interface of the attachment mechanism 115 at the first sheath 105 to the second slope region 260b. The first slope region 260a can have a greater slope than the second slope region 260b. In one such specific example, the first slope region 260a and the second slope region 260b, forming the first attachment mechanism step-up dilation 252a, can together resemble a "bullnose" geometry from a side-elevational vantage point with the first slope region 260a forming the greater slope portion of the "bullnose" and the second slope region 260b forming the lesser slope portion of the "bullnose." For instance, the first attachment mechanism step-up dilation 252a can be defined (e.g., by the combination of the first and second slope regions 260a, 260b) such that the first attachment mechanism step-up dilation radial height 258 is greater in magnitude than the first attachment mechanism step-up dilation longitudinal length 255. Namely, in various embodiments, the first attachment mechanism step-up dilation radial height 258 can be 0.254 to 1.27 cm, 0.508 to 1.016 cm, or 0.635 to 0.889 cm (e.g., 0.635 cm), and the first attachment mechanism step-up dilation longitudinal length 255 can be 0.254 to 0.635 cm, 0.3175 to 0.5715 cm, or 0.381 to 0.508 cm (e.g., 0.4445 cm).

With respect to the second attachment mechanism step-up dilation 252b, for example, the second slope of the second attachment mechanism step-up dilation 252b can be greatest at a location proximate the distal-most interface with the first sheath 105 and decrease in a direction moving proximally toward the second sheath 110. For instance, the second slope of the second attachment mechanism step-up dilation 252b can be defined by the than the second attachment mechanism step-up dilation longitudinal length 256, which can be less than the first attachment mechanism step-up dilation longitudinal length 255, and the second attachment mechanism step-up dilation radial height 259, which can be less than the first attachment mechanism step-up dilation radial height 258. In the specific example, where the first attachment mechanism step-up dilation 252a is configured to resemble a "bullnose," the second attachment mechanism step-up dilation 252b can have a different configuration, such a parabolic, linear, or beveled edge configuration. In some examples, the second attachment mechanism step-up dilation 252b can form a portion of the attachment mechanism step-up dilation 252 that is symmetrical about the first sheath 105, while the first attachment mechanism step-up dilation 252a can form a remaining portion of the attachment mechanism step-up dilation 252 that is asymmetrical about the first sheath 105.

The attachment mechanism step-up dilation 252, including the first attachment mechanism step-up dilation 252a and/or the second attachment mechanism step-up dilation 252b, can form a generally rigid outer surface at the attachment mechanism 115 (e.g., at the distal-most portion of the attachment mechanism 115). For example, the attachment mechanism step-up dilation 252, including the first attachment mechanism step-up dilation 252a and/or the second attachment mechanism step-up dilation 252b, can form an outer surface at the attachment mechanism 115 that has a Shore A Hardness between 30 and 100, 40 and 95, 40 and 90, 50 and 95, 50 and 90, or 80-85. The outer surface at the attachment mechanism 115 including the attachment mechanism step-up dilation 252 can be made of one or more of a variety of materials with the noted Shore A Hardness range. As one example, the outer surface at the attachment mechanism 115 including the attachment mechanism step-up dilation 252 can include polyurethane with a Shore A Hardness between 30 and 100, 40 and 95, 40 and 90, 50 and 95, 50 and 90, or 80-85. Configuring the attachment mechanism step-up dilation 252 to form the generally rigid outer surface at the attachment mechanism 115 can help to reduce instances of "fish-mouthing," or stretching of the material, at the outer surface of the attachment mechanism 115. This, in turn, can help to reduce instances of a gap forming between components of the sheath assembly 100 (e.g., a gap forming between the first sheath 105 and the attachment mechanism 115) which could catch or interfere with the vessel wall at the single access site 155 when the sheath assembly 100 is being introduced into the vessel.

The attachment mechanism step-up dilation 252 can terminate at a proximal end of the first attachment mechanism step-up dilation longitudinal length 255, and proximal of the termination of the proximal end of the first attachment mechanism step-up dilation longitudinal length 255 can be an attachment mechanism non-dilation region 261 at the attachment mechanism 115. The attachment mechanism non-dilation region 261 can define a region of the attachment mechanism 115 along which the cross-sectional diameter (e.g., longitudinal cross-sectional diameter 246) of the attachment mechanism 115 is generally constant. The attachment mechanism non-dilation region 261 can have an attachment mechanism non-dilation region longitudinal length 262 that extends from the proximal end of the first attachment mechanism step-up dilation longitudinal length 255, where the first attachment mechanism step-up dilation 252a terminates, toward the second sheath 110. The cross-sectional diameter (e.g., longitudinal cross-sectional diameter 246) of the attachment mechanism 115 can be generally constant along the attachment mechanism non-dilation region longitudinal length 262. In some such examples, the attachment mechanism non-dilation region longitudinal length 262, of the attachment mechanism non-dilation region 261, can extend from the proximal end of the first attachment mechanism step-up dilation longitudinal length 255, where the first attachment mechanism step-up dilation 252a terminates, to the distal-most end of the second sheath 110. In various embodiments, the attachment mechanism non-dilation region longitudinal length 262 can be, for instance, at least 5 cm, at least 8 cm, at least 10 cm, at least 12 cm, at least 15 cm, at least 20 cm, at least 25 cm, or at least 30 cm. The presence of the attachment mechanism non-dilation region 261, and thus the noted attachment mechanism non-dilation region longitudinal length 262, can be sufficiently long enough to allow the vessel, at the single access site 155, enough time during the sheath assembly 100 introduction, to relax and settle, uncurl any folds that may have formed at the vessel wall during introduction of the attachment mechanism step-up dilation 252 at the single access site 155, and bounce back to the initial shape experienced at the outset of sheath assembly 100 introduction before the vessel, at the single access site 155, encounters the second sheath 110.

As noted, the attachment mechanism non-dilation region 261 at the attachment mechanism 115 can lead to the distal-most end of the second sheath 110. As shown in the illustrated embodiment, the second sheath 110 can include a second sheath step-up dilation 265. The second sheath step-up dilation 265 can be included at the second sheath 110 at the distal-most end of the second sheath 110 such that, for example, the second sheath step-up dilation 265 begins where the attachment mechanism non-dilation region 261 terminates. Moving proximally from the attachment mechanism non-dilation region 261, the second sheath step-up dilation 265 can be configured to additionally increase the profile of the sheath assembly 100 from that of the attachment mechanism 115. The second sheath step-up dilation 265 can be configured to be the next component, after the attachment mechanism non-dilation region 261, of the sheath assembly 100 to encounter the single access site 155 as the sheath assembly 100 continues to be introduced into the vessel. The second sheath 110 can include the second sheath step-up dilation 265 beginning at the distal-most end of the second sheath 110 where the second sheath interfaces with the attachment mechanism 115. The second sheath step-up dilation 265 can be configured to increase a cross-sectional diameter (e.g., longitudinal cross-sectional diameter 246) along a second sheath step-up dilation longitudinal length 266 moving proximally from the distal-most longitudinal location where the second sheath 110 interfaces with the attachment mechanism 115. In particular, the second sheath 110 can have a smallest cross-sectional diameter (e.g., longitudinal cross-sectional diameter 246) at the distal-most end of the second sheath 110 where the second sheath 110 interfaces with the attachment mechanism 115, and the second sheath step-up dilation 265 can extend, along the second sheath step-up dilation longitudinal length 266, from this smallest cross-sectional diameter (e.g., longitudinal cross-sectional diameter 246) at the distal-most end of the second sheath 110 where the second sheath 110 interfaces with the attachment mechanism 115 along the second sheath step-up dilation longitudinal length 266 in a proximal direction toward the proximal hub 125.

The second sheath step-up dilation 265 can be configured to increase the cross-sectional diameter (e.g., longitudinal cross-sectional diameter 246), along the second sheath step-up dilation longitudinal length 266, via an offset wall arrangement at the second sheath opening 149. For example, as shown in the illustrated embodiment, the second sheath 110 can have a first distal wall portion 267 forming a first portion of the second sheath opening 149 at a location adjacent the attachment mechanism 115 and a second distal wall portion 268 forming a second portion of the second sheath opening 149 at a location opposite the attachment mechanism 115. The first distal wall portion 267 can more distally located on the sheath assembly 100 than the second distal wall portion 267, such that, for instance, the first distal wall portion 267 can be closer to the introducer 161 than the second distal wall portion 268. The second sheath step-up dilation 265 can be configured to increase the cross-sectional diameter between the first distal wall portion 267 and the second distal wall portion 268 and along the second sheath step-up dilation longitudinal length 266. The longitudinally offset wall arrangement of first distal wall portion 267 and the second distal wall portion 268 can facilitate the increase in the cross-sectional diameter between the first distal wall portion 267 and the second distal wall portion 268 created by the second sheath step-up dilation 265 in a relatively gradual manner. For example, an angle $\ominus$ can be defined relative to the first sheath central longitudinal axis 106, and the angle $\ominus$ can define the slope, or rate or increase in cross-sectional diameter, between the first distal wall portion 267 and the second distal wall portion 268 over the second sheath step-up dilation longitudinal length 266. In various examples, the angle $\ominus$ can be between ten degrees and eighty degrees, between fifteen degrees and seventy degrees, between twenty and sixty degrees, or between twenty-five and fifty degrees.

A second sheath step-up dilation radial height 269 (e.g., extending out from the outer surface of the attachment mechanism 115), of the second sheath 110, can be formed between the first distal wall portion 267 and the second distal wall portion 268. As noted, the longitudinally offset wall arrangement of first distal wall portion 267 and the second distal wall portion 268 can facilitate the relatively gradual increase in the cross-sectional diameter, created by the second sheath step-up dilation 265, up to the second sheath step-up dilation radial height 269. The second sheath step-up dilation radial height 269 can vary depending on whether the second sheath 110 is in the expanded state or the collapsed state. When the second sheath 110 is in the expanded state, as shown in FIGS. 4 and 5, the second sheath step-up dilation radial height 269 can be between 1 mm and 5 mm, for example between 1.5 mm and 4.5 mm, 2 mm and 4.5 mm, or 2.5 mm and 4.0 mm. When the second sheath 110 is in the collapsed state, the second sheath step-up dilation radial height 269 can be less than 1 mm, such as less than 0.75 mm, less than 0.67 mm, less than 0.5 mm, or less than 0.3 mm. The longitudinally offset wall arrangement of first distal wall portion 267 and the second distal wall portion 268 can facilitate the relatively gradual increase in the cross-sectional diameter, created by the second sheath step-up dilation 265, can be present both when the second sheath 110 is in the expanded configuration and when the second sheath 110 is in the collapsed configuration. And, to facilitate the ability of the second sheath 110 to transition between the expanded and collapsed configurations, the second sheath 110 can have a second hardness and the attachment mechanism 115 and/or the first sheath 105 can have a first hardness that is greater than the second hardness, for instance as described previously herein. The second sheath 110 can be configured to be biased to the expanded state and configured to transition from the expanded state to the collapsed state when the second sheath comes into contact with a vessel wall. This configuration of the second sheath 110 to transition from the greater second sheath step-up dilation radial height 269 in the expanded state to the lesser second sheath step-up dilation radial height 269 in the collapsed state can help to reduce an area at the distal-most end of the second sheath that can be susceptible to catching, or snagging onto, the vessel wall when the sheath assembly is inserted at the single access site 155 and, thereby, help to facilitate a more efficient sheath assembly introduction process while at the same time providing the ability to deliver addition device payload via the second sheath 110 when transitioned into the expanded state after insertion at the single access site 155.

Referring to FIG. 5 in particular, the illustrated embodiment shows a portion of the sheath assembly 100 that can be symmetrical about the first sheath longitudinal axis 106 and another portion of the sheath assembly 100 can be asymmetrical about the first sheath longitudinal axis 106. For example, the introducer 161 and the first sheath 105 can be symmetrical about the first sheath longitudinal axis 106, while at least a portion of the attachment mechanism 115 and the second sheath 110 can be asymmetrical about the first sheath longitudinal axis 106. More particularly, the second attachment mechanism step-up dilation 252b, of the attachment mechanism step-up dilation 252 at the attachment mechanism 115, can be symmetrical about the first sheath longitudinal axis 106, while the first attachment mechanism step-up dilation 252a, of the attachment mechanism step-up dilation 252 at the attachment mechanism 115, can be asymmetrical about the first sheath longitudinal axis 106. This can configure the first attachment mechanism step-up dilation 252a to be "out of round" relative to the other portions of the attachment mechanism 115, including the second attachment mechanism step-up dilation 252b. In addition to the first attachment mechanism step-up dilation 252a, the second sheath 110 can be asymmetrical about the first sheath longitudinal axis 106. More particularly, the second sheath step-up dilation 265 can extend away from the first sheath longitudinal axis 106 at a same side of the sheath assembly 100 where the first attachment mechanism step-up dilation 252a is located. Thus, as seen in the example at FIG. 5, the asymmetrical, relative to the first sheath longitudinal axis 106, first attachment mechanism step-up dilation 252a and second sheath step-up dilation 265 can be at a same side of the sheath assembly 100. Yet, other portions of the sheath assembly 100 can be symmetrical relative to the first sheath longitudinal axis 106, including one or more sides of the sheath assembly offset from the side of the sheath assembly 100 having the attachment mechanism step-up dilation 252 and the second sheath step-up dilation 265.

Also illustrated at the example of FIG. 5 is a connection interface 270 between the attachment mechanism 115 and the second sheath 110. The sheath assembly 100 can include the connection interface 270 between the attachment mechanism 115 and the second sheath 110 such that no gap is present between the attachment mechanism 115 and the second sheath 110. More specifically, the attachment mechanism 115 can include an outer attachment mechanism surface 271 and the second sheath 110 can include an outer surface 272. The outer surfaces 271, 272 can be coupled together in a manner that excludes an air gap between the attachment mechanism 115 and the second sheath 110 at the connection interface 270. This can be particularly useful where air gaps are excluded between the attachment mechanism 115 and the second sheath 110 at the connection interface between the first distal wall portion 267 of the second sheath 10 and the outer attachment mechanism surface 271 since this can reduce instances where the vessel wall can become snagged during insertion of the sheath assembly at the single access site 155.

To further help prevent such vessel wall snagging at the second sheath 110, at least a portion 272a of the second sheath outer surface 272, such as the portion 272a extending way from the first sheath longitudinal axis 106, can be tangent to the outer attachment mechanism surface 271. For example, the attachment mechanism 115 can include an upper half portion 115a defined above a plane 275 that extends perpendicular to the first sheath longitudinal axis 106. The portion 272a, of the second sheath outer surface 272, extending way from the first sheath longitudinal axis 106 can be tangent to a point 271a that is located both at the outer attachment mechanism surface 271 and at the upper half portion 115a. In some such examples, the portion 272a, of the second sheath outer surface 272, extending way from the first sheath longitudinal axis 106 can have a radius of curvature equal to a radius of curvature at the point 271a that is located both at the outer attachment mechanism surface 271 and at the upper half portion 115a. As such, the portion 272a can extend away from the outer attachment mechanism surface 271 in a configuration that maintains a gap-free interface at the connection interface 270 between the outer attachment mechanism surface 271 and the second sheath outer surface 272. In a further such example, the portion 272a can continue to extend away from the outer attachment mechanism surface 271 in the noted configuration to a point 273 that is located at an upper half portion of the second sheath 110, where the upper half portion of the second sheath 110 can be defined as an upper half of the second sheath step-up dilation radial height 269 in the expanded state furthest away from the attachment mechanism 115.

To also help facilitate delivery of the sheath assembly 100 via the single access site 155, the second sheath 110 can be smaller than the first sheath 105, the attachment mechanism 115, and/or the combination of the first sheath 105 and the attachment mechanism 115. For instance, the second sheath 110, when in the expanded state, can define a cross-sectional area that is less than half of a cross-sectional area defined by the first sheath 105, the attachment mechanism 115, and/or the combination of the first sheath 105 and the attachment mechanism 115. In a more specific such instance, the second sheath 110, when in the expanded state, can define a cross-sectional area that is less than a third of a cross-sectional area defined by the first sheath 105, the attachment mechanism 115, and/or the combination of the first sheath 105 and the attachment mechanism 115.

Figure 6:
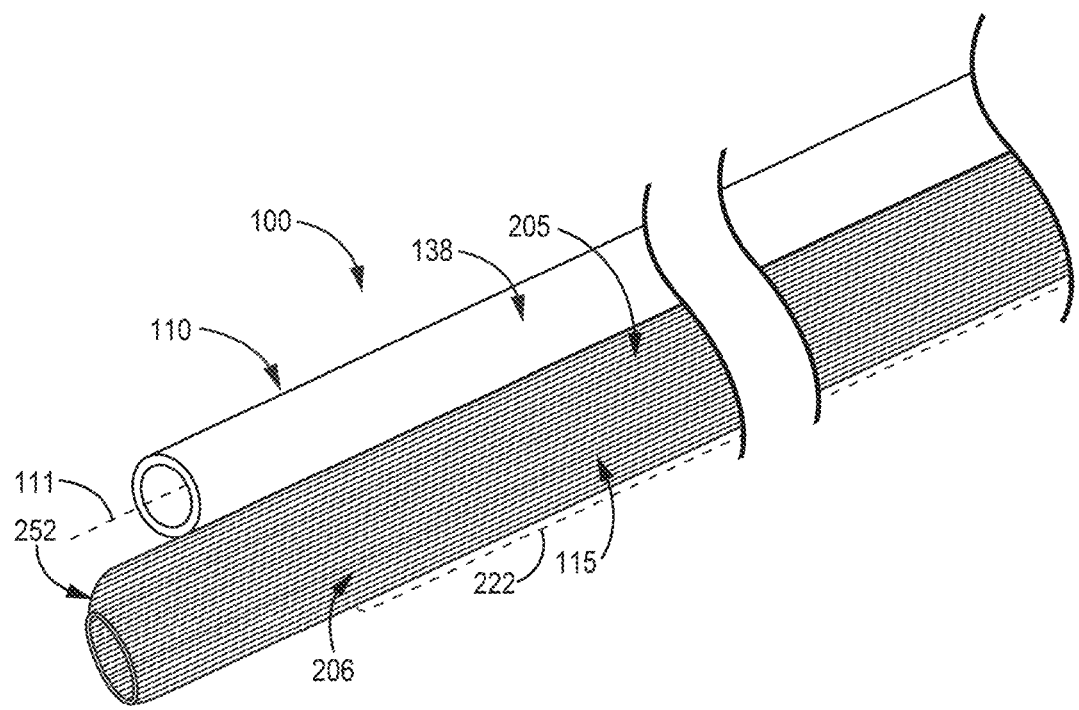
FIG. 6 is an isolated, perspective view of the second sheath and attachment mechanism of the sheath assembly embodiment of FIG. 1.

FIG. 6 illustrates an isolated, perspective view of the second sheath 110 and the attachment mechanism 115 of the sheath assembly 100. The second sheath 110 can be coupled to the attachment mechanism 115, and the attachment mechanism 115 can secure the second sheath 110 to the first sheath such that a first portion of the second sheath 110 outer surface interfaces with a portion of the first sheath outer surface. For the illustrated embodiment, the attachment mechanism 115 can be said to be configured to secure the second sheath 110 to the first sheath in a stacked arrangement. In this illustrated embodiment, the attachment mechanism 115 does not pass over the second sheath 110, but rather the attachment mechanism 115 is generally in contact with the second sheath 110 at only the first portion of the second sheath outer surface interfacing with the first sheath outer surface. This arrangement of the attachment mechanism 115 can be useful in securing the second sheath 110 to the first sheath while not constraining the ability of the second sheath 110 to transition between the expanded and collapsed states.

In the illustrated embodiment, the attachment mechanism 115 is in the form of an elastic band. As shown, the second portion of the second sheath outer surface can be free of the elastic band, which as noted can facilitate the transitioning of the second sheath 110 between the expanded and collapsed states. In the illustrated embodiment, the elastic band is configured to extend around the entire first sheath outer surface for a particular longitudinal length along the first sheath longitudinal axis 106. The elastic band can be configured to stretch so as to increase the area defined within the elastic band (e.g., the interior lumen defined by inner surface 206 of the attachment mechanism 115). This can be useful in securing the second sheath 110 to the first sheath 105, since in some instances the first sheath outer surface can have one or more geometric irregularities that necessitate the elastic band to expand in order to pass over such irregularities. As such, the expandable nature of the elastic band can be useful in allowing the second sheath 110 to be added on to a variety of first sheaths while also providing a sufficient securement force to maintain the second sheath 110 in place relative to the first sheath 105.

As noted, the attachment mechanism 115 includes the attachment member inner surface 206. The attachment member inner surface 206 can define a lumen at which the first sheath is received. The attachment member inner surface 206 can be configured to impart a frictional force at a first sheath outer surface sufficient to prohibit relative movement between the first sheath and the second sheath 110. For example, the attachment mechanism inner surface 206 can be configured to impart the frictional force at the first sheath outer surface sufficient to prohibit relative movement between the first sheath and the second sheath 110 upon an insertion force applied to the sheath assembly 100 of up to 15 lbf (pound-force), up to 12 lbf, up to 10 lbf, up to 8 lbf, up to 5 lbf, or up to 3 lbf. The insertion force applied at the sheath assembly 100 can vary depending on the application (e.g., the size of the first sheath 105 and/or the second sheath 110, the anatomical location of the access site 155, the vessel 150 within which the sheath assembly is advanced), and the attachment mechanism inner surface 206 can be configured to impart the frictional force at the first sheath outer surface sufficient to prohibit relative movement between the first sheath and the second sheath 110 upon the particular insertion force expected to be applied to the sheath assembly 100 in the particular application.

The attachment mechanism 115 also includes an attachment mechanism outer surface 205. The attachment mechanism outer surface 205 can be coupled to the interfacing outer surface 138 of the second sheath 110. As one example, the attachment mechanism outer surface 205 can be coupled to the interfacing outer surface 138 of the second sheath 110 via a welded connection where the attachment mechanism outer surface 205 interfaces with the outer surface 138 of the second sheath 110. As seen best in the embodiment of FIG. 5, the welded connection between the attachment mechanism outer surface 205 and the outer surface 138 of the second sheath 110 can be present about less than 50%, less than 40%, less than 35%, less than 30%, or less than 25% of the circumference of the outer surface 138 of the second sheath 110 at a given cross-sectional location where the second sheath 110 is coupled to the attachment mechanism 115.

In some embodiments, the welded coupling of the second sheath 110 to the attachment mechanism 115 can help to facilitate the asymmetrical cross-sectional profile of the attachment mechanism 115 relative to the first sheath central longitudinal axis 106. For instance, melting the second sheath 110 to the attachment mechanism 115 outer surface 205, can cause surface tension to be increased at the outer surface 205 of the attachment mechanism 115. This increased surface tension at the outer surface 205 of the attachment mechanism 115 can be of a force magnitude sufficient to pull a portion of the attachment mechanism 115, interfacing with the second sheath 110, away from the first sheath central longitudinal axis 106. This increased surface tension can thus pull the portion of the attachment mechanism 115 interfacing with the second sheath 110 "out of round" relative to the first sheath central longitudinal axis 106 and thereby configure the attachment mechanism 115 in the asymmetrical cross-sectional profile, such as that shown in FIGS. 4 and 5. This coupling of the interfacing potion of the outer surface 205 of the attachment mechanism 115 can, in some instances, be referred to as a reflow manufacturing process.

In the illustrated embodiment, the attachment mechanism 115 can include a perforation 222. The attachment mechanism 115 can be configured to break along the perforation 222, such as when the first sheath expands. The perforation 222 can be included along the outer surface 205 of the attachment mechanism 115, for instance at a location of the outer surface 205 opposite the portion of the outer surface 205 interfacing with the second sheath 110 and, in many cases, the perforation 222 can also be opposite the asymmetrical portion of the attachment mechanism 115. And, the perforation 222 can extend along the outer surface 206 in a direction parallel to the second sheath central longitudinal axis 111. When the perforation 222 breaks, the attachment mechanism 115 can change from a continuous loop to a generally "C" shaped band, allowing the attachment mechanism 115 to accommodate the increase in size of the first sheath while still maintaining the second sheath 110 secured to the first sheath.

The embodiment of the sheath assembly 100 is illustrated to include one of the second sheath 110. In other additional embodiments, the sheath assembly 100 can include two or more of the second sheath 110. For example, in one such additional embodiment, the sheath assembly 100 can include two of the second sheath 110, for instance spaced apart about the outer circumference of the attachment mechanism 115 (e.g., at opposite locations of one another about the outer circumference of the attachment mechanism 115). As another example, in another such additional embodiment, the sheath assembly 100 can include a plurality of second sheaths 110 distributed around the outer circumference of the attachment mechanism 115.

In these additional embodiments that include two or more second sheaths 110, one or more the various features (e.g., each of the various features) disclosed herein, with respect to the illustrated sheath assembly 100 single second sheath 110 embodiment, can be included at the second sheath 110 and the attachment mechanism 115. For example, in additional embodiments where the sheath assembly includes two or more second sheaths 110, the first sheath 105 can include the first sheath step-up dilation 250, the attachment mechanism 115 can include the attachment mechanism step-up dilation 252 and the attachment mechanism non-dilation region 261 aligned with the location of each second sheath 110, and each second sheath 110 can include the second sheath step-up dilation 265. In particular, as noted, these additional embodiments, the attachment mechanism step-up dilation 252 and the attachment mechanism non-dilation region 261 can be included at the attachment mechanism 115 at a location aligned, circumferentially about the outer surface of the attachment mechanism 115, with the circumferential location of each of the second sheaths 110. For instance, in an embodiment where the sheath assembly includes two second sheaths 110 at opposite locations about the outer circumference of the attachment mechanism 115, the attachment mechanism step-up dilation 252 and the attachment mechanism non-dilation region 261 can be included at these opposite circumferential locations at the outer surface of the attachment mechanism 115. Similarly, in an embodiment where the sheath assembly include two second sheaths 110 positioned adjacent one another at the outer circumference of the attachment mechanism 115, the attachment mechanism step-up dilation 252 and the attachment mechanism non-dilation region 261 can be included at these adjacent circumferential locations at the outer surface of the attachment mechanism 115 (e.g., such that the attachment mechanism step-up dilation 252 and the attachment mechanism non-dilation region 261 are continuous about these adjacent locations along the outer circumference of the attachment mechanism 115).

Figure 7:
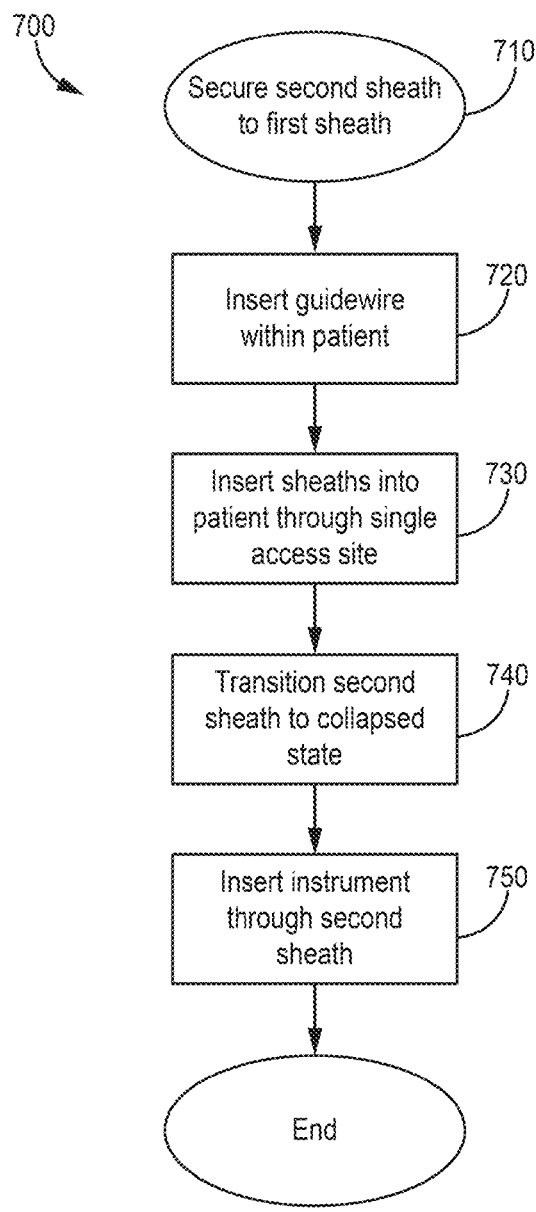
FIG. 7 is a flow diagram of an embodiment of a method of using a sheath assembly.

FIG. 7 is a flow diagram of an embodiment of a method 700 of using a sheath assembly. For example, the sheath assembly referenced in the method 900 can be similar to, or the same as, the sheath assembly 100 disclosed elsewhere herein.

At step 710, the method 700 includes the step of securing a second sheath to a first sheath to form the sheath assembly. The second sheath in the method 700 can be similar to, or the same as, the second sheath 110 disclosed herein. The first sheath in the method 700 can be similar to, or the same as, the first sheath 105 disclosed herein. Step 710 could include removing the second sheath from a packaging container and securing the second sheath to the first sheath via one or more attachment members, such as the attachment mechanism 115. This could include securing the attachment member around the outer surface of the first sheath while a majority of the outer surface of the second sheath remains free of the attachment member. Step 710 can also include securing the second sheath to the first sheath using the attachment member where the attachment member includes both a symmetrical cross-sectional portion (e.g., symmetrical about the first sheath central longitudinal axis) and an asymmetrical cross-sectional portion (e.g., asymmetrical about the first sheath central longitudinal axis). The second sheath can be secured to the first sheath such that the symmetrical cross-sectional portion of the attachment mechanism is spaced apart from (e.g., located opposite) the second sheath and the asymmetrical cross-sectional portion of the attachment mechanism is located at the interface with the second sheath.

At step 720, the method 700 includes the step of inserting a guidewire within a patient. The guidewire can be inserted within a vessel lumen and advanced to a region of interest via a single access site at the patient. The guidewire can be inserted within the vessel lumen at step 720 after performing an interventional technique to puncture the target vessel to create an opening for guidewire insertion at the single access site.

At step 730, the method 700 includes the step of inserting the sheath assembly—e.g., the first and second sheaths coupled together via the noted attachment mechanism—into the patient through a single access site. For example, the first sheath can be placed onto the guidewire and the first and second sheath can be interested together, along with the attachment mechanism, through the single access site into a vessel lumen and advanced through the vessel lumen to a region of interest.

In some embodiments, inserting the sheath assembly at step 730 can include contacting the vessel wall, defining the vessel lumen at the single access site, first with the first sheath step-up dilation (e.g., the first sheath step-up dilation 250), then subsequently with the attachment mechanism step-up dilation (e.g., the attachment mechanism step-up dilation 252), such as the first attachment mechanism step-up dilation (e.g., the first attachment mechanism step-up dilation 252a) followed by the second attachment mechanism step-up dilation (e.g., the second attachment mechanism step-up dilation 252b), then subsequently with the attachment mechanism non-dilation region (e.g., the attachment mechanism non-dilation region 261), and then subsequently with the second sheath step-up dilation (e.g., the second sheath step-up dilation 265). As described elsewhere herein, this insertion sequence at the single access site, facilitated by the configuration of the sheath assembly, can help to allow for a more efficient insertion process of the sheath assembly at the single access site (e.g., by allowing the vessel, at the single access site, enough time to relax and settle, uncurl any folds that may have formed at the vessel wall during introduction of a portion of the sheath assembly, and bounce back to the initial shape experienced at the outset of sheath assembly introduction prior to introducing another, greater cross-sectional diameter portion of the sheath assembly).

At step 740, the method 700 includes the step of transitioning the second sheath from an expanded state to a collapsed state. For example, the second sheath can transition from the expanded state to the collapsed state when the second sheath comes into contact with the vessel wall defining the vessel lumen into which the first and second sheaths are inserted and advanced. The second sheath can transition to the collapsed state as a result of a force imparted in a first direction by the vessel wall on the second sheath outer surface and a force imparted in a second opposite direction by the first sheath outer surface. Transitioning the second sheath to the collapsed state can result in reducing the profile of the sheath assembly within the vessel lumen (e.g., and bringing at least a portion of the second sheath closer to the attachment mechanism, such as closer to the asymmetrical portion of the attachment mechanism). This can be useful in allowing the sheath assembly to be used via a single access site at the patient.

At step 750, the method 700 includes the step of inserting an instrument through the second sheath. The instrument can be inserted through the lumen of the second sheath. The instrument can be, for instance, a diagnostic and/or interventional instrument, such as a diagnostic and/or interventional catheter (e.g., pigtail catheter and associated guidewire within the second sheath). The step of inserting the instrument through the second sheath can cause the second sheath to transition from the collapsed state toward the expanded state. Namely, inserting the instrument within the lumen of the second sheath can impart a force on the second sheath inner surface that counteracts the force imparted by the vessel wall on the second sheath outer surface so as to expand the second sheath outward away from the first sheath and toward the vessel wall. Notably, in this way, the second sheath can be transitioned from the collapsed state toward the expanded state only to the extent needed to accommodate the instrument within the second sheath lumen, thereby keeping a minimum necessary profile of the sheath assembly even when an instrument is actively being used in the second sheath lumen during a procedure. Accordingly, transitioning the second sheath between expanded and collapsed states can facilitate a reduced profile of the sheath assembly both during insertion and placement as well as during usage of the second sheath during a procedure, in turn allowing the sheath assembly to be capable of use via the single access site.

In some instances, the method 700 can further include, after step 750, steps of removing the instrument from the lumen of the second sheath and then removing the sheath assembly from the from the patient. For example, the step of removing the instrument from the lumen of the second sheath can transition the second sheath from the expanded state to the collapsed state. Namely, as described previously, without the instrument within the lumen of the second sheath the second sheath can be configured to collapse when in contact with the vessel wall as a result of the forces imparted on the second sheath outer surface by each of the vessel wall and the first sheath. Then, with the second sheath in the collapsed state, the sheath assembly can be removed from the vessel. Removing the sheath assembly from the vessel can include removing both of the first sheath and the second sheath, as well as the attachment mechanism, together over the guidewire. With the second sheath in the collapsed state, the sheath assembly can be removed from the vessel while in a more reduced, compact profile relative to when the sheath assembly is at the region of interest and the instrument is within the lumen of the second sheath.

Various non-limiting exemplary embodiments have been described. It will be appreciated that suitable alternatives are possible without departing from the scope of the examples described herein. These and other examples are within the scope of the following claims.

What is claimed is:

1. A method of using a sheath assembly, the method comprising the steps of:
   inserting a guidewire to a region of interest within a patient;
   placing a first sheath, of the sheath assembly, over the guidewire and inserting the first sheath and a second sheath, of the sheath assembly, into the patient through a single access site at the patient, wherein the sheath assembly comprises:
   the first sheath comprising a first sheath first end portion, a first sheath second end portion opposite the first sheath first end portion, a first sheath inner surface, and a first sheath outer surface opposite the first sheath inner surface, the first sheath inner surface defining a first sheath lumen extending along a first sheath longitudinal axis between the first sheath first end portion and the first sheath second end portion, the second sheath, and an attachment mechanism coupled to the first sheath and configured to secure the first sheath to the second sheath, wherein, when the attachment mechanism secures the first sheath to the second sheath, the attachment mechanism includes a first attachment mechanism step-up dilation at a first attachment mechanism portion and a second attachment mechanism step-up dilation at a second attachment mechanism portion, the second attachment mechanism step-up dilation being different than the first attachment mechanism step-up dilation, wherein, when the attachment mechanism secures the first sheath to the second sheath, the attachment mechanism includes a first longitudinal cross-sectional profile, at the first attachment mechanism portion, that is asymmetrical about a longitudinal axis of the second sheath, wherein, when the attachment mechanism secures the first sheath to the second sheath, the attachment mechanism includes a second longitudinal cross-sectional profile, at the second attachment mechanism portion, that is symmetrical about the longitudinal axis of the second sheath, wherein the first attachment mechanism portion interfaces with the first sheath outer surface, and wherein the second attachment mechanism portion is opposite the first sheath;

contacting the single access site with at least one of the first attachment mechanism step-up dilation and the second attachment mechanism step-up dilation and then with the second sheath;

transitioning the second sheath from an expanded state to a collapsed state upon inserting the second sheath into the patient, the second sheath collapsing to the collapsed state in a direction toward the first sheath; and inserting an instrument through the second sheath and causing the second sheath to transition from the collapsed state to the expanded state.

2. The method of claim 1, further comprising:
after contacting the single access site with at least one of the first attachment mechanism step-up dilation and the second attachment mechanism step-up dilation and before contacting the single access site with the second sheath, contacting the single access site with an attachment mechanism non-dilation region.

3. The method of claim 2, wherein the attachment mechanism non-dilation region defines a portion of the attachment mechanism along which a cross-sectional diameter of the attachment mechanism is constant.

4. The method of claim 3, wherein, when the attachment mechanism secures the first sheath to the second sheath, the attachment mechanism non-dilation region of the attachment mechanism is located longitudinally between the first attachment mechanism step-up dilation and a distal-most end of the first sheath.

5. The method of claim 4, wherein the attachment mechanism non-dilation region extends along a non-dilation region longitudinal length from a proximal end of the first attachment mechanism step-up dilation to the distal-most end of the first sheath, and wherein the non-dilation region longitudinal length is at least 5 cm.

6. The method of claim 4, wherein, when the attachment mechanism secures the first sheath to the second sheath, the first sheath includes a first sheath step-up dilation, and wherein the first sheath step-up dilation is included at a distal-most end of the first sheath interfacing with the attachment mechanism non-dilation region.

7. The method of claim 1, wherein, when the attachment mechanism secures the first sheath to the second sheath, each of the first attachment mechanism step-up dilation and the second attachment mechanism step-up dilation is located between the first sheath and the second sheath.

8. The method of claim 7, further comprising:
after contacting the single access site with each of the first attachment mechanism step-up dilation and the second attachment mechanism step-up dilation and before contacting the single access site with the second sheath, contacting the single access site with an attachment mechanism non-dilation region.

9. The method of claim 8, wherein the attachment mechanism non-dilation region defines a portion of the attachment mechanism along which a cross-sectional diameter of the attachment mechanism is constant.

10. The method of claim 1, wherein the first attachment mechanism portion and the second attachment mechanism portion are included at a common longitudinal location on the attachment mechanism.

11. The method of claim 1, wherein, when the attachment mechanism secures the first sheath to the second sheath, the first attachment mechanism step-up dilation has a first slope that is defined by a first attachment mechanism step-up dilation longitudinal length and a first attachment mechanism step-up dilation radial height, wherein, when the attachment mechanism secures the first sheath to the second sheath, the second attachment mechanism step-up dilation has a second slope that is defined by a second attachment mechanism step-up dilation longitudinal length and a second attachment mechanism step-up dilation radial height, and wherein the second slope is different than the first slope.

12. The method of claim 11, wherein, when the attachment mechanism secures the first sheath to the second sheath, the first attachment mechanism step-up dilation radial height is at a side of the attachment mechanism facing the first sheath and the second attachment mechanism step-up dilation radial height is at another side of the attachment mechanism opposite the first sheath, and wherein, when the attachment mechanism secures the first sheath to the second sheath, the first attachment mechanism step-up dilation radial height is greater than the second attachment mechanism step-up dilation radial height.

13. The method of claim 11, wherein, when the attachment mechanism secures the first sheath to the second sheath, the first slope of the first attachment mechanism step-up dilation is greatest at a location proximate a distal-most interface between the attachment mechanism and the second sheath, and wherein, when the attachment mechanism secures the first sheath to the second sheath, the first slope of the first attachment mechanism step-up dilation decreases in a direction moving proximally toward the first sheath.

14. The method of claim 13, wherein, when the attachment mechanism secures the first sheath to the second sheath, the first slope of the first attachment mechanism step-up dilation includes a first slope region and a second slope region, wherein the first slope region has a greater slope magnitude than the second slope region, wherein the first slope region is distal of the second slope region, and wherein the first slope region extends a portion of the first attachment mechanism step-up dilation longitudinal length from the distal-most interface between the attachment mechanism and the second sheath to the second slope region.

15. The method of claim 14, wherein the first attachment mechanism step-up dilation radial height is greater than the first attachment mechanism step-up dilation longitudinal length.

16. The method of claim 14, wherein the first attachment mechanism step-up dilation radial height is between 0.254 to 1.27 cm, and wherein the first attachment mechanism step-up dilation longitudinal length is between 0.254 to 0.635 cm.

17. The method of claim 1, wherein, when the attachment mechanism secures the first sheath to the second sheath, an angle, defined relative to the longitudinal axis of the second sheath, is between fifteen and seventy five degrees.

18. A method of using a sheath assembly, the method comprising the steps of:
  inserting a guidewire to a region of interest within a patient;
  placing a sheath assembly over the guidewire and inserting the sheath assembly into the patient through a single access site at the patient, wherein the sheath assembly comprises:
    a first sheath comprising a first sheath first end portion, a first sheath second end portion opposite the first sheath first end portion, a first sheath inner surface, and a first sheath outer surface opposite the first sheath inner surface, the first sheath inner surface defining a first sheath lumen extending along a first sheath longitudinal axis between the first sheath first end portion and the first sheath second end portion, wherein the first sheath is configured to transition between an expanded state and a collapsed state, wherein the first sheath is biased to the expanded state,
    a second sheath, and
    an attachment mechanism coupled to the first sheath and configured to secure the first sheath to the second sheath, wherein, when the attachment mechanism secures the first sheath to the second sheath, the attachment mechanism includes a first attachment mechanism step-up dilation at a first attachment mechanism portion and a second attachment mechanism step-up dilation at a second attachment mechanism portion, the second attachment mechanism step-up dilation being different than the first attachment mechanism step-up dilation;
  contacting the single access site with at least one of the first attachment mechanism step-up dilation and the second attachment mechanism step-up dilation and then with the second sheath;
  transitioning the first sheath from the expanded state to the collapsed state by overcoming the bias of the first sheath to the expanded state upon contact between the first sheath outer surface and a vessel wall defining a vessel lumen at the single access site at the patient to thereby transition the first sheath to the collapsed state in a direction toward the attachment mechanism; and
  inserting an instrument through the first sheath to cause the first sheath to transition from the collapsed state to the expanded state.

19. The method of claim 18, wherein, when the attachment mechanism secures the first sheath to the second sheath, the attachment mechanism includes a first longitudinal cross-sectional profile, at the first attachment mechanism portion, that is asymmetrical about a longitudinal axis of the second sheath, wherein, when the attachment mechanism secures the first sheath to the second sheath, the attachment mechanism includes a second longitudinal cross-sectional profile, at the second attachment mechanism portion, that is symmetrical about the longitudinal axis of the second sheath, wherein the first attachment mechanism portion interfaces with the first sheath outer surface, and wherein the second attachment mechanism portion is opposite the first sheath.

20. The method of claim 18, wherein, when the attachment mechanism secures the first sheath to the second sheath, the first attachment mechanism step-up dilation has a first slope that is defined by a first attachment mechanism step-up dilation longitudinal length and a first attachment mechanism step-up dilation radial height, wherein, when the attachment mechanism secures the first sheath to the second sheath, the second attachment mechanism step-up dilation has a second slope that is defined by a second attachment mechanism step-up dilation longitudinal length and a second attachment mechanism step-up dilation radial height, and wherein the second slope is different than the first slope.

* * * * *